US008471013B2

(12) United States Patent
Ovadia et al.

(10) Patent No.: US 8,471,013 B2
(45) Date of Patent: Jun. 25, 2013

(54) PROCESS FOR THE PREPARATION OF SUBSTITUTED CYANOPHENOXY-PYRIMIDINYLOXY-PHENYL ACRYLATE DERIVATIVES

(75) Inventors: David Ovadia, Omer (IL); Raya Sturkovich, Beer-Sheva (IL); David Leonov, Rehovot (IL)

(73) Assignee: Makhteshim Chemical Works, Ltd. (IL)

( * ) Notice: Subject to any disclaimer, the term of this patent is extended or adjusted under 35 U.S.C. 154(b) by 361 days.

(21) Appl. No.: 12/519,436

(22) PCT Filed: Dec. 16, 2007

(86) PCT No.: PCT/IL2007/001551
§ 371 (c)(1),
(2), (4) Date: Jun. 16, 2009

(87) PCT Pub. No.: WO2008/075341
PCT Pub. Date: Jun. 26, 2008

(65) Prior Publication Data
US 2009/0281316 A1 Nov. 12, 2009

(30) Foreign Application Priority Data

Dec. 17, 2006 (IL) .......................................... 180134

(51) Int. Cl.
*C07D 239/54* (2006.01)
*C07D 213/30* (2006.01)
*C07C 43/205* (2006.01)

(52) U.S. Cl.
USPC ........... 544/319; 544/335; 546/290; 546/306; 568/630; 568/716; 570/182

(58) Field of Classification Search
USPC ........... 544/319, 335; 546/290, 306; 568/639, 568/716; 570/182
See application file for complete search history.

(56) References Cited

U.S. PATENT DOCUMENTS

| | | | |
|---|---|---|---|
| 4,708,734 A | 11/1987 | Hayashi et al. | |
| 5,145,856 A | 9/1992 | Clough et al. | |
| 5,395,837 A | 3/1995 | Clough et al. | |
| 5,760,250 A | 6/1998 | Jones et al. | |
| 6,153,750 A | 11/2000 | Whitton et al. | |
| 6,162,916 A | 12/2000 | Whitton et al. | |
| 6,162,945 A | 12/2000 | Keil et al. | |
| 7,084,272 B2 * | 8/2006 | Jackson et al. ................. 544/319 |
| 2002/0042514 A1 | 4/2002 | Doyle et al. | |
| 2004/0092746 A1 | 5/2004 | Clough et al. | |
| 2004/0242607 A1 | 12/2004 | Jackston et al. | |
| 2006/0160272 A1 | 7/2006 | Effenberger et al. | |
| 2006/0229450 A1 | 10/2006 | Jackson et al. | |
| 2008/0214587 A1 | 9/2008 | Whitton et al. | |
| 2010/0036124 A1 | 2/2010 | Beveridge et al. | |

FOREIGN PATENT DOCUMENTS

| | | |
|---|---|---|
| CN | 1234794 A | 10/1997 |
| EP | 0053306 A1 | 6/1982 |
| EP | 0242081 A1 | 10/1987 |
| IN | 179039 | 2/1994 |
| JP | 8-512046 | 12/1996 |
| WO | WO92/08703 A1 | 5/1992 |
| WO | 9501326 | 1/1995 |
| WO | 9701538 | 1/1997 |
| WO | 9807707 | 2/1998 |
| WO | WO98/18767 | 5/1998 |
| WO | 2004026305 | 4/2004 |
| WO | 2004113419 A2 | 12/2004 |
| WO | 2006/103694 | 10/2006 |
| WO | 2006114572 A2 | 11/2006 |
| WO | 2008043977 A1 | 4/2008 |
| WO | WO2008/093325 A2 | 8/2008 |

OTHER PUBLICATIONS

European Patent Office, PCT International Search Report, International Application No. PCT/IL2007/001551, Date of Mailing: May 16, 2008.
European Search Report, dated Oct. 30, 2012, for EP12179669, 11 pages.

* cited by examiner

*Primary Examiner* — Venkataraman Balasubramanian
(74) *Attorney, Agent, or Firm* — Cantor Colburn LLP

(57) ABSTRACT

The present invention provides a process for reacting between a phenol derivative and an aromatic substrate under phenolate forming conditions comprising the following steps: (a) reacting a phenol derivative with a base in a polar organic solvent to obtain a phenolate salt, wherein water is removed form the reaction mixture during the reaction, (b) adding the aromatic substrate to the reaction mixture obtained in step (a), (c) heating the reaction mixture of step (b) to a temperature in the range of 80° to 1300° C., preferably, 90° to 1000° C. for 2 to 7 hours to obtain a phenoxy substituted aromatic substrate, (d) removing the solvent from the mixture of step (c) and optionally further isolating an purifying the phenoxy substituted aromatic substrate. Optionally, the removal of water during step (a) is in conjunction with partial removal of the organic solvent.

18 Claims, No Drawings

US 8,471,013 B2

PROCESS FOR THE PREPARATION OF SUBSTITUTED CYANOPHENOXY-PYRIMIDINYLOXY-PHENYL ACRYLATE DERIVATIVES

FIELD OF THE INVENTION

The present invention relates to the field of chemical synthesis, particularly to improved processes for synthesizing substituted cyanophenoxy-pyrimidinyloxy-phenyl acrylate derivatives.

BACKGROUND OF THE INVENTION

In the field of industrial chemical synthesis, the improvement of the yield and selectivity of chemical processes bears considerable impact on the industry. Particularly, the focus in said improvements is on lowering costs, simplifying unit operations and environmental considerations. These three factors are particularly important in the field of agrochemicals where the volume of chemicals is large and the marginal profit is relatively small.

Of the many agrochemical compounds which are synthesized by multi-stage synthesis, methyl (E)-2-{2-[6-(2-cyanophenoxy)pyrimidin-4-yloxy]phenyl}-3-methoxyacrylate (chemical common name: azoxystrobin), particularly drew the attention of the present inventors. Azoxystrobin, disclosed in U.S. Pat. No. 5,395,837, is a plant protection fungicide with protectant, curative, eradicant, translaminar and systemic properties. The preparation of azoxystrobin as described in Example 3 of U.S. Pat. No. 5,395,837 involves an aromatic substitution reaction between 2-cyanophenol and (E)-Methyl 2-[2-(6-chlorpyridimin-4-yloxy)phenyl]-3-methoxypropenoate also known as (E)-Methyl-2-[2-(6-chloropyrimidin-4-yloxy)-phenyl]-3-methoxyacrylate, at temperatures at 95° to 100° C. in DMF in the presence of stoichiometric amounts of potassium carbonate and a catalytic amount of copper(I) chloride. The reported yield of azoxystrobin is 65% wherein the product was found to have a melting point of 110° C.-111° C., indicating a final product of relatively low purity, which subsequently required further purification. It has been suggested that reactions of 2-cyanophenol or other isomers of cyanophenol or phenols in general under conditions of temperatures of about 90° C. and above, in the presence of basic reagents which can promote the formation of phenolate salts, may cause polymerization and the formation of tars. This clearly is a highly undesirable side effect.

Accordingly there is an ongoing and long felt need for a process for aromatic substitution reactions in the presence phenols with improved yield and selectivity.

Thus, it is the objective of the present invention to provide a process for reacting phenols under basic conditions in which the yield and selectivity is improved.

Other objectives of the invention shall become apparent as the description proceeds.

SUMMARY OF THE INVENTION

The present invention provides a process for reacting between a phenol derivative and an aromatic substrate under phenolate forming conditions comprising the following steps:

a) reacting a phenol derivative with a base in a polar organic solvent to obtain a phenolate salt, wherein water is removed from the reaction mixture during the reaction.

b) adding the aromatic substrate to the reaction mixture obtained in step (a), c) heating the reaction mixture of step (b) to a temperature in the range of 80° to 130° C., preferably, 90-100° C. for 2 to 7 hours to obtain a phenoxy substituted aromatic substrate, d) removing the solvent from the mixture of step (c) and further isolating and purifying the phenoxy substituted aromatic substrate.

Optionally, the removal of water during step (a) is in conjunction with partial removal of the organic solvent.

DETAILED DESCRIPTION OF THE INVENTION

The following description is illustrative of embodiments of the invention. The following description is not to be construed as limiting, it being understood that the skilled person may carry out many obvious variations to the invention. Throughout the specification the terms "phenols" and "phenol derivative" include phenol and mono and poly-substituted phenols, including 2-cyanophenol and other cyanophenol isomers.

The present invention provides a process for reacting between a phenol derivative and an aromatic substrate under phenolate forming conditions wherein the formation of polymeric by-products and tars are minimized. In minimizing said by-products and tars formation, the present process provides improved yields together with facilitation of product separation and purification. The present process provides yields of 90% and greater, wherein said yield is calculated on the basis of the aromatic substrate. It has been surprisingly found that generating the phenolate salt separately and subsequently reacting said phenolate salt with the aromatic substrate, prevents the formation of undesirable by-products and tars.

The present process comprises the following steps:

a) reacting a phenol derivative with a base in a polar organic solvent to obtain a phenolate salt, wherein water is removed from the reaction mixture during the reaction.

Step (a) is conducted wherein the mole ratio between said phenol derivative and base is preferably between 1:1 to 1:1.5, preferably 1:1.125 to 1:1.15. The time required for step (a) to obtain conversion to a phenolate salt is 30 to 120 minutes at a temperature between 60° C. to 80° C., while partially removing solvent with water from the reaction mixture by vacuum distillation.

According to a preferred embodiment of the present invention said phenol derivative may be phenol, mono-substituted phenol or poly-substituted phenol, more preferably, cyanophenol derivatives, including 2-cyanophenol and 4-cyanophenol.

Said base may be selected from among hydroxide and carbonate bases, including but not limited to metal hydroxides, alkali metal hydroxides, metal carbonates and alkali metal carbonates preferably, sodium hydroxide or potassium hydroxide.

Non-limiting examples of preferred polar organic solvents are dimethyl formamide (DMF), dimethyl acetamide (DMAA) and dimethyl sulphoxide (DMSO) wherein, preferably the range of the reagent/solvent ratio is 0.1 mole/150 ml-0.1 mole/350 ml.

According to a specific embodiment of the invention, the phenolate salt is formed via partial removal of solvent with water under reduced pressure conditions.

b) adding the aromatic substrate to the reaction mixture obtained in step (a).

According to a particular embodiment of the invention said aromatic substrate may be added together with a polar organic solvent selected from the afore-mentioned group of solvents.

The aromatic substrate is added in an amount such that the mole ratio between the phenol derivative and aromatic substrate is between 1:0.8 and 1:1

In yet a further preferred embodiment of the invention, the aromatic substrate is selected from among mono and poly-substituted pyridine, pyrimidine and phenyl groups. Preferably, at least mono-halo substituted and more preferably chloro-pyrimidine derivatives.

c) heating the reaction mixture of step (b) to a temperature in the range of 80° to 130° C., preferably about 100° C. for 2 to 7 hours, preferably about 5 hours to obtain a phenoxy substituted aromatic substrate,
  d) removing the solvent from the mixture of step (c) and further isolating and purifying the phenoxy substituted aromatic substrate.

The operations of step (d) can be carried out according to methods known to the skilled artisan. Said methods include; solvent removal by distillation wherein said distillation may be carried out under reduced pressure conditions, separation and purification by washing, extraction and crystallization.

According to a specific preferred embodiment of the present invention, there is provided a process for the preparation of methyl (E)-2-{2-[6-(2-cyanophenoxy)pyrimidin-4-yloxy]phenyl}-3-methoxyacrylate (azoxystrobin) comprising of the following steps:

a) reacting 2-cyanophenol with an alkali metal hydroxide or carbonate, preferably sodium hydroxide in a polar organic solvent preferably selected from among DMF, DMAA and DMSO, more preferably DMAA, at a temperature between 60° C. to 80° C., preferably between 60° C. to 70° C. for about 1 hour, while removing the water which is formed during the reaction via distillation with the solvent under reduced pressure, preferably about 20-30 mbar. The mole ratio between 2-cyanophenol and alkali metal hydroxide is between 1:1 and 1:1.5.
  b) adding the aromatic substrate which is (E)-Methyl 2-[2-(6-chloropyridimin-4-yloxy)phenyl]-3-methoxypropenoate (Compound of formula (I) to the reaction mixture obtained in step (a). Optionally. Compound (I) is added to the reaction mixture as a solution in DMAA.

(I)

c) heating the reaction mixture of step (b) to a temperature in the range of 80° to 130° C., preferably 90° C. to 100° C. for 2 to 7 hours, preferably 4 to 6 hours to obtain azoxystrobin,
  d) removing the solvent from the mixture of step (c) by distillation under reduced pressure; and further washing and extracting the reaction mixture with a non-polar organic solvent, non-limiting examples being toluene, xylene, at least $C_4$ acetate esters, preferably, butylacetate and adding water to obtain an organic and aqueous phase, thereafter discarding the aqueous phase and crystallizing the azoystrobin from the organic phase by cooling the organic solvent, filtering the precipitated solid and rinsing thereafter with an alcohol, preferably methanol to obtain azoxystrobin with purity of 98%-99%.

In yet a further specific embodiment of the present invention azoxystrobin is prepared according to the following process:
  a) reacting 2-cyanophenol with sodium hydroxide in DMAA and DMSO, more preferably DMAA, at a temperature between 60° C. to 80° C. for about 1 hour, while removing the water which is formed during the reaction via distillation with the solvent under reduced pressure of about 20-30 mbar, wherein the mole ratio between 2-cyanophenol and sodium hydroxide is between 1:1 and 1:1.5;
  b) adding the aromatic substrate which is (E)-Methyl 2-[2-(6-chlorpyridimin-4-yloxy)phenyl]-3-methoxypropenoate (Compound of formula (I) to the reaction mixture obtained in step (a), wherein Compound (I) is added to the reaction mixture as a solution in DMAA.

(I)

c) heating the reaction mixture of step (b) to a temperature in the range of 90° C. to 100° C. for 4 to 6 hours to obtain azoxystrobin,
  d) removing the solvent from the mixture of step (c) by distillation under reduced pressure; and further washing and extracting the reaction mixture with butylacetate and adding water to obtain an organic and aqueous phase, thereafter discarding the aqueous phase and crystallizing the azoxystrobin from the organic phase by cooling the organic solvent, filtering the precipitated solid and rinsing thereafter with methanol to obtain azoxystrobin with purity of 98%-99%.

The process for obtaining azoxystrobin according to the present invention provided azoxystrobin with purity of 98%-99% and a yield of above 90%. This is a significant improvement in comparison to the prior art methods which describe a process with a yield of 64%. Furthermore, no tars were detected in the reaction mixture of the present invention unlike the prior art method which generates tars which affect the purity of the final product. Hence the process of the present invention is more economical, produces less by-products and impurities and further generates considerably less effluents as a result of the improved yield. Accordingly, the work up according to the present process thus the process also provides improvements in terms of environmental and working safety.

EXAMPLES

Example I

Preparation of Azoxystrobin

Dimethylacetamide (DMAA, 400 ml), 2-Cyanophenol (0.2M, 28 g) and NaOH (0.225M, 9 g) were placed at ambient temperature into the three-necked 1 L flask equipped with stirrer, condenser and thermometer. Half the amount of DMAA containing water traces was distilled at vacuum 20 mbar/60-65° C. and the mixture was kept at vacuum 20 mbar/room temperature for 1 h. The same amount of prime DMAA was added and Compound (I) (0.2M, 64 g) was fed into the flask.

The reaction mixture was heated to 100° C. and kept at these conditions for 5 hours (monitored by HPLC-conversion of Compound (I) to Azoxystrobin 98-99%).

DMAA was distilled at vacuum 20 mbar/65-70° C. At the end of the distillation the temperature can be increased up to 90-100° C.

400 g Butylacetate (BuAc) and 200 g water were added to the reaction mixture at 50-60° C., the temperature was increased to 80° C. and stirred 10-15 min. The water phase was separated at 80° C. to remove DMAA traces and inorganic salts.

For crystallization the BuAc phase was slowly cooled from 80° C. to −5° C. Filtration was done using filter #2. The cake was washed with 60 ml cooled Butylacetate or methanol and further dried in oven at 80° C. during 15 hours. Azoxystrobin with purity 98-99% and a yield of 90-92% was obtained.

While embodiments of the invention have been described by way of illustration, it will be apparent that the invention may be carried out with many modifications, variations and adaptations, without departing from its spirit or exceeding the scope of the claims.

The invention claimed is:

1. A process for reacting a cyanophenol derivative and an aromatic substrate, wherein the aromatic substrate is selected from the group consisting of mono- and poly-substituted pyridine, pyrimidine and phenyl groups, each substituted with a halogen, under phenolate forming conditions comprising the following steps:
  a) reacting a cyanophenol derivative with a base in a polar organic solvent to obtain a phenolate salt, wherein water is removed from the reaction mixture during the reaction,
  b) adding the aromatic substrate to the reaction mixture comprising the phenolate salt obtained in step (a),
  c) heating the reaction mixture of step (b) to a temperature in the range of 80° to 130° C. for 2 to 7 hours to obtain a phenoxy substituted aromatic substrate,
  d) removing the solvent from the mixture of step (c) comprising the phenoxy substituted aromatic substrate.

2. A process according to claim 1, wherein the removal of water during step (a) is in conjunction with partial removal of the polar organic solvent.

3. A process according to claim 1, wherein the mole ratio between said cyanophenol derivative and base is 1:1 to 1:1.5.

4. A process according to claim 1, wherein the time required for step (a) to obtain conversion to the phenolate salt is 30 to 120 minutes at a temperature between 60° C. to 80° C., while partially removing solvent with water from the reaction mixture by vacuum distillation.

5. A process according to claim 1, wherein the cyanophenol derivative is selected from 2-cyanophenol and 4-cyanophenol.

6. A process according to claim 1, wherein said base is selected from the group consisting of a hydroxide, a carbonate base, and a combination thereof.

7. A process according to claim 1, wherein the polar organic solvent is selected from the group consisting of dimethyl formamide (DMF), dimethyl acetamide (DMAA), dimethyl sulphoxide (DMSO), and a combination thereof, and further wherein the reagent/solvent ratio is 0.1 mole/150 ml to 0.1 mole/350 ml.

8. A process according to claim 1, wherein said aromatic substrate is added in step (b) together with a polar organic solvent.

9. A process according to claim 1, wherein the aromatic substrate is added in an amount such that the mole ratio between the phenol derivative and aromatic substrate is between 1:0.8 and 1:1.

10. A process according to claim 1, comprising heating the reaction mixture of step (b) to a temperature in the range of 80° to 130° C. for 2 to 7 hours to obtain the phenoxy substituted aromatic substrate.

11. A process according to claim 1 for the preparation of methyl (E)-2-{2-[6-(2-cyanophenoxy)pyrimidin-4-yloxy]phenyl}-3-methoxyacrylate (azoxystrobin) comprising the following steps:
  a) reacting 2-cyanophenol with an alkali metal hydroxide or carbonate, in a polar organic solvent, at a temperature between 60° C. to 80° C., for about 1 hour, while removing the water which is formed during the reaction via distillation with the solvent under reduced pressure,
  b) adding (E)-methyl 2-[2-(6-chlorpyridimin-4-yloxy)phenyl]-3-methoxypropenoate of formula (I) to the reaction mixture obtained in step (a),

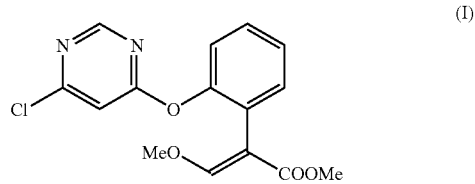 [SMILES: CO/C=C(/C(=O)OC)c1ccccc1Oc1cc(Cl)ncn1]

(I)

c) heating the reaction mixture of step (b) to a temperature in the range of 80° to 130° C., for 2 to 7 hours, to obtain azoxystrobin,
  d) removing the solvent from the mixture of step (c) by distillation under reduced pressure to obtain a crude azoxystrobin,
  e) extracting the crude azoxystrobin with a non-polar organic solvent and water to obtain an organic and aqueous phase, and
  f) crystallizing the azoxystrobin from the organic phase by cooling the organic solvent, filtering the precipitated solid and rinsing the precipitated solid with an alcohol to obtain azoxystrobin with a purity of 98%-99%.

12. A process according to claim 11, wherein said base is sodium hydroxide, potassium hydroxide, sodium carbonate or potassium carbonate.

13. A process according to claim 11, wherein said polar organic solvent is selected from the group consisting of dimethyl formamide (DMF), dimethyl acetamide (DMAA), dimethyl sulphoxide (DMSO), and a combination thereof.

14. A process according to claim 11, wherein removing the water which is formed during the reaction of step (a) is via distillation with the solvent under reduced pressure, wherein the mole ratio between the 2-cyanophenol and the base is between 1:1 and 1:1.5.

15. A process according to claim 11, wherein said non-polar organic solvent of step (e) is selected from the group consisting of toluene, xylene, at least $C_4$ acetate esters, and a combination thereof.

16. A process according to claim 11, further comprising:
  a) reacting the 2-cyanophenol with sodium hydroxide in DMAA, DMSO, or a combination thereof, at a temperature between 60° C. to 80° C. for about 1 hour, while removing the water which is formed during the reaction via distillation with the solvent under a reduced pressure of about 20-30 mbar, wherein the mole ratio between the 2-cyanophenol and the sodium hydroxide is between 1:1 and 1:1.5;

b) adding (E)-methyl 2-[2-(6-chlorpyridimin-4-yloxy) phenyl]-3-methoxypropenoate of formula (I) as a solution in DMAA to the reaction mixture obtained in step (a), c) heating the reaction mixture of step (b) to a temperature in the range of 90° C. to 100° C. for 4 to 6 hours to obtain azoxystrobin, d) removing the solvent from the mixture of step (c) by distillation under reduced pressure to obtain a crude azoxystrobin, e) extracting the crude azoxystrobin with butylacetate and water to obtain an organic and aqueous phase, and f) crystallizing the azoxystrobin from the organic phase by cooling the organic solvent, filtering the precipitated solid and rinsing the precipitated solid with methanol to obtain azoxystrobin with a purity of 98%-99%.

17. The process according to claim 6, wherein the base is selected from the group consisting of including metal hydroxides, alkali metal hydroxides, metal carbonates, alkali metal carbonates, and mixtures thereof.

18. The process according to claim 1, wherein the aromatic substrate is a chloro-pyrimidine derivative.

* * * * *